(12) United States Patent
Zozulya et al.

(10) Patent No.: US 8,396,676 B2
(45) Date of Patent: Mar. 12, 2013

(54) METHOD AND DEVICE FOR MEASURING VISCO-ELASTIC FLUID PARAMETERS

(75) Inventors: Oleg Mikhailovich Zozulya, Moscow (RU); Igor Borisovich Esypov, Moscow (RU); Andrey Viktorovich Fokin, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 304 days.

(21) Appl. No.: 12/947,258

(22) Filed: Nov. 16, 2010

(65) Prior Publication Data

US 2011/0130980 A1 Jun. 2, 2011

(30) Foreign Application Priority Data

Nov. 16, 2009 (RU) ................................ 2009141894

(51) Int. Cl.
*G01F 17/00* (2006.01)
(52) U.S. Cl. ......................................................... 702/50
(58) Field of Classification Search ................... 702/50, 702/54
See application file for complete search history.

(56) References Cited

U.S. PATENT DOCUMENTS 7,162,915 B2 * 1/2007 Drahm et al. ................ 73/54.24
7,552,619 B2 6/2009 Andle

* cited by examiner

*Primary Examiner* — Stephen Cherry

(57) ABSTRACT

The invention relates to measuring visco-elastic fluid parameters, in particular, in the oil production industry, for defining heavy oil parameters during field development.
The method involves the excitation of a hollow resonance device oscillations by sending a continuous variable-frequency signal to two transmitting transducers located on the outer surface the said resonance device. Oscillations are recorded by a receiving transducer. Amplitude-vs-frequency response curve is plotted and effective resonance frequency $\omega_r$ is determined. Thereafter, a cavity of the said resonance device is filled with a medium under examination, and oscillations are excited to obtain associated amplitude-vs-frequency response values. An axially symmetric capacity placed in a thermostabilized chamber is used as the resonance device. While implementing the method, the attenuation factor $\alpha$ is also determined for the empty and test medium-filled resonance device as well as the resonance frequency shift $\Delta\omega_r$ and the attenuation variance $\Delta\alpha$ re determined in relation to the hollow resonance device.

16 Claims, 9 Drawing Sheets

METHOD AND DEVICE FOR MEASURING VISCO-ELASTIC FLUID PARAMETERS

FIELD OF THE INVENTION

The present invention relates to methods and devices for measuring visco-elastic fluid parameters, specifically, for measuring viscosity and elasticity of a fluid sample, using a resonance rod method while studying acoustic properties of fluids, and may be used, in particular, in the oil production industry, for defining heavy oil parameters during field development. In this regard, studying visco-elastic properties of heavy oils dependent on their temperature, in combination with oil field thermal recovery technologies, is of special interest.

Therefore, the claimed method and device may be used for all fluid-saturated (derived from the English word fluid—flowing medium) non-consolidated (lack of integral unifying structure; the meaning is opposite to the "consolidated" term (lat.)—consolidatio, derived from the word con (cum)—together, conjointly and solido—compact, strengthen, merge, reinforcement/strengthening of something) media, i.e., essentially, for any visco-elastic medium, which may be placed in a tube, provided that at least satisfactory contact between the medium and the said tube is ensured, in particular, for suspensions (dispersed solutions, jellies), etc.

BACKGROUND OF THE INVENTION

An acoustic logging method, i.e. a method for studying formation properties based on borehole measurements of elastic wave properties in a frequency range of 5-20 kHz, is a commonly used technique for well survey and development. However, visco-elastic properties of heavy oils in a frequency range that is typical for acoustic logging cannot be determined by using standard rheometric devices (laboratory instrumentation), whose operating range is within 0.001-100 Hz. This is why it is necessary to develop adequate devices and methods to perform adequate measurements of visco-elastic properties in the acoustic logging frequency range, in particular, in a broad range of temperatures.

A resonance method for measuring density, viscosity and visco-elastic properties of fluid is described in U.S. Pat. No. 7,552,619. The above-mentioned method uses a resonance device that is designed as two electromechanically connected resonators and is characterized by a frequency curve with two closely located poles, which correspond to symmetrical and antisymmetrical oscillation modes. Two closely positioned peaks on the resonance curve refer to these poles. The method includes the excitation of a hollow resonance device oscillations by sending a continuous variable-frequency signal to, at least, two transmitting transducers located at the outer surface of the said resonance device, with a recording of oscillations by at least one receiving transducer, located on the outer surface of the resonance device, with a follow-up plotting of an amplitude-vs-frequency response curve, and determination of the effective resonance frequency $\omega_r$, the filling of a cavity of the resonance device with a medium under examination; the excitation of medium-filled resonance device oscillations by sending a continuous variable-frequency signal to the transmitting transducers with a follow-up pick-up of amplitude-vs-frequency response curve and determination of viscosity and visco-elastic properties based on the modified functions, which take into account measured data.

Difficulties in the resonance device fabrication, which increases capital expenditures required for the implementation of the method, is a disadvantage of the above-mentioned method. At the same time, a great number of acoustic surfaces (due to the resonance device complexity) cause uncontrolled spurious resonances, thus reducing the efficiency of the measuring system and the accuracy of the method as a whole.

SUMMARY OF THE INVENTION

This invention aims to to develop a fast-response method for measuring visco-elastic fluid parameters—modulus of elasticity and viscosity—at reduced capital expenditures, improved measurement accuracy in a broad range of temperatures; these goals constitute the claimed technical result to be achieved.

In addition, an additional technical result is the possibility to implement a method for measuring visco-elastic fluid properties at acoustic logging frequencies, in particular, 5-20 kHz.

The claimed technical result is reached through the excitation of a hollow resonance device by sending a continuous variable-frequency signal to, at least, two transmitting transducers located at the outer surface of the resonance device, with a recording of oscillation values by at least one receiving transducer, located on the outer surface of the resonance device, with a follow-up determination of the amplitude-vs-frequency response values. Based on the function received, effective resonance frequency $\omega_r$ is defined. Thereafter, a cavity of the resonance device is filled with a test medium and the medium-filled resonance device is excited by sending a continuous variable-frequency signal to the transmitting transducers, and associated amplitude-vs-frequency response values are received. While implementing the method, torsional oscillations are excited. Amplitude-vs-frequency response values are determined by the first oscillation mode. An axially symmetric resonance device is placed in a thermostabilized chamber. Dimensions and materials of the resonance device are selected so as to minimize the impact of oscillation modes, which differ from the effective resonance. While implementing the method, the attenuation ratio $\alpha$ of the empty and test medium-filled resonance device, resonance frequency shift $\Delta\omega_r$ and the attenuation variance $\Delta\alpha$ are determined in relation to the hollow resonance device. The below mentioned formula is applied to calculate the real part of the shear modulus $\mu$ and dynamic viscosity $\eta$:

$$\eta_f(\omega_r)\rho_f = \frac{\Delta\omega_r \Delta\alpha}{2\omega_r}(\rho_s R_1((R_2/R_1)^4 - 1))^2,$$

$$\mu_f(\omega_r)\rho_f = \frac{\Delta\alpha^2 - \Delta\omega_r^2}{4}(\rho_s R_1((R_2/R_1)^4 - 1))^2,$$

where $\omega_r$—resonance frequency value for an empty capacity (no fluid), $\Delta\omega_r$—resonance frequency shift, $\Delta\alpha$—attenuation variance, $\rho$—density, $R_1$ & $R_2$—inner and outer radiuses of the capacity, respectively; lower indices f and s refer to fluid and capacity, respectively.

The above-mentioned technical result is also reached through a diametrically opposed positioning of transmitting transducers on the resonance device's side wall at the bottom level.

An additional technical result, associated with the possibility of implementation of the method at a required effective resonance frequency, e.g., at a value taken from the acoustic logging frequency range (5-20 kHz), is reached through defining absolute dimensions of the resonance device—length, inner and outer radius—at the established relationship between them and a selected material of the tube (characterized, first of all, by Young's modulus and shear modulus).

The claimed technical result is also reached through the implementation of a device for measuring visco-elastic fluid parameters, which comprises a resonance device that comprises at least two transmitting transducers and at least one receiving transducer, both located on the resonance device's outer surface. The device also includes a computer and a sine wave generator & an analog-to-digital converter, all connected to the computer, wherein an input of the analog-to-digital converter is connected to a receiving converter, whilst the output of the said sine wave generator is connected to the transmitting transducers. The device is provided with a thermostabilized chamber, in which the resonance device is positioned vertically, being hanged along the line of the node of the first mode of torsional oscillations. The resonance device is axially symmetric, whose dimensions and material are selected so as to minimize the impact of oscillation modes, which differ from the effective resonance. A tube may be used as the axially symmetric resonance device.

Transmitting transducers are positioned diametrically opposed to each other on the resonance device's side wall at the bottom level. The receiving transducer is positioned on the resonance device's side wall, at the bottom level, at a distance equally remote from the transmitting transducers. The receiving transducer is connected to the input of the analog-to-digital (A/D) converter via a signal amplifier.

The thermostabilized chamber is of an air type. The thermostabilized chamber is made with a cylinder-shaped side wall. The side wall is hollow and is filled with a cooling fluid. The thermostabilized chamber is provided with a microfan. The thermostabilized chamber is provided with a temperature transducer connected to a thermostat.

Absolute dimensions of the resonance device are defined at the established relationship between its length and inner & outer radius for a selected material.

BRIEF DESCRIPTION OF THE FIGURES

The claimed invention is explained by the following drawings:

DETAILED DESCRIPTION

Figure 1:
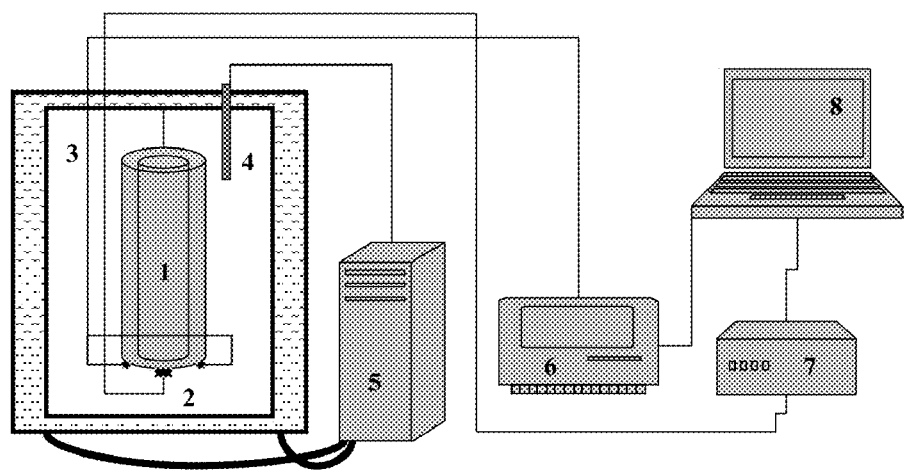
FIG. 1—Experimental unit for measuring shear visco-elastic fluid properties in a temperature range, FIG. 2—Rated amplitude/frequency response vs temperature curve for a 150 mm-long hollow tube. The curves are numbered in increasing order of a temperature: 1° C. (1), 5° C. (2), 10° C. (3), 15° C. (4), 20° C. (5), 30° C. (6), 40° C. (7) and 60° C. (8)), FIG. 3—Variation dependent on amplitude-and-frequency response temperature for a 150 mm-long tube filled with glycerin. The curves are numbered in increasing order of a temperature: 1° C. (1), 5° C. (2), 10° C. (3), 15° C. (4), 20° C. (5), 30° C. (6), 40° C. (7) and 60° C. (8), FIG. 4—Frequency offset and attenuation vs temperature curve for glycerin, FIG. 5—Glycerin shear viscosity vs reverse absolute temperature, FIG. 6—Variation dependent on amplitude-and-frequency response temperature for a 75 mm-long tube filled with oil. The curves are numbered in increasing order of a temperature: −9.3° C. (1), −4.7° C. (2), 1° C. (3), 5° C. (4), 10° C. (5), 15° C. (6), 20° C. (7), 30° C. (8), 40° C. (9) and 60° C. (10), FIG. 7—Frequency & attenuation ratio variation vs temperature for oil, FIG. 8—Temperature-variant function of the real part and imaginary part of the shear modulus for the Mordovo-Karmalskoye field oil, FIG. 9—Temperature-variant function of the real part and imaginary part of the shear modulus for the Mordovo-Karmalskoye field oil.
Figure 2:
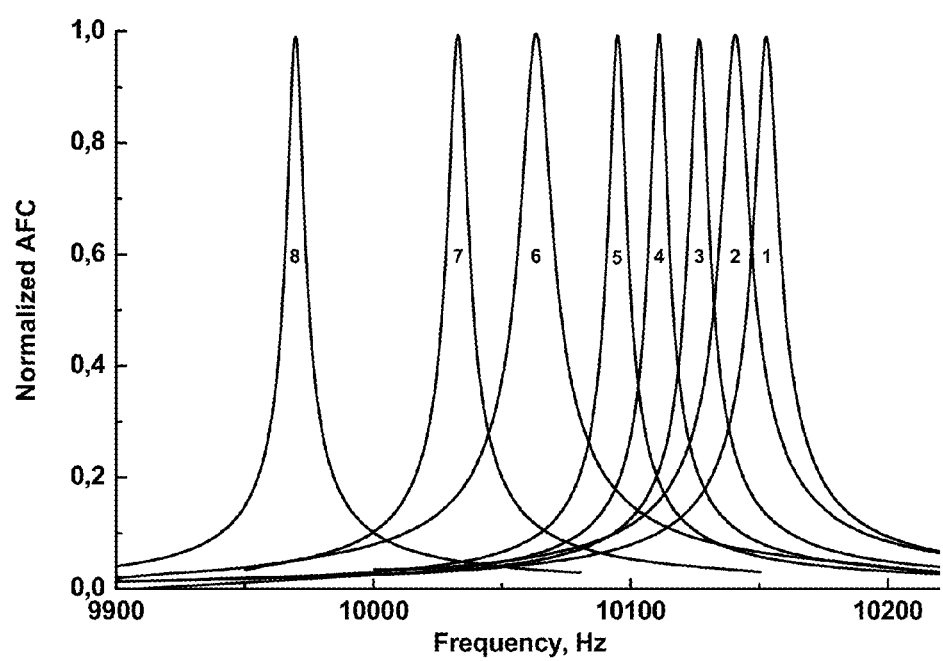

Methods for measuring acoustic wave velocity and attenuation in high viscosity materials may be split in reflectometry methods, impulse methods, waveguide-impedance methods as well as resonance methods, which are based on measuring a resonance frequency shift and the oscillation factor-of-merit variance for the resonator during its contact with fluid under examination. Hereinafter, within the frames of the claimed engineering solution, any axially symmetric vessel (e.g., a tube) will be assumed as a "resonance device".

The developed method is a modification of the resonance rod method that calls for determination of a visco-elastic modulus through measuring a resonance frequency and a factor-of-merit (reciprocal of the attenuation coefficient) of a certain mode of natural oscillations of a sample-filled tube at increased measurement accuracy.

In regard to the sample factor-of-merit, the following should be mentioned. The factor-of-merit is a parameter of an oscillating system, which defines the resonance sharpness and indicates how many times the energy reserves in the oscillator's reactive elements are greater than the energy loss at active elements for one oscillation cycle. The factor-of-merit is inversely proportional to a natural oscillation attenuation rate of the system. i.e., the higher the factor-of-merit of a resonance system, the lower the energy losses in each period. Oscillations in a system with a high factor-of-merit attenuate slowly. In other words, the factor-of-merit is defined, first of all, by a specimen material and, in case of a high factor-of-merit, is characterized, first of all, by "narrow peaks" of the effective resonance as well as by the fact that the effective resonance is far away from resonances of other oscillation modes ($2^{nd}$, $3^{rd}$ and other modes) and other spurious resonances on the resonance curve. Certainly, this situation is typical, to a great extent, for solid homogenous materials, whose factor-of-merit is typically high. In this regard, for example, in accordance with a resonance ultrasonic spectroscopy (RUS) method which is applicable to solid materials, it's possible to unambiguously determine elasticity modulus G based on ultrasonic emission.

While studying visco-elastic fluids, the above-mentioned method cannot be implemented in full, since these media are characterized by a low factor-of-merit—<<overstretched peaks>> in the resonance curve, interference of spurious resonance and other modes of oscillations onto effective resonances. In this case, it is necessary to develop methods which take into account peculiarities of a medium under study.

It's common knowledge that a complex shear modulus of fluid is expressed as follows: $G_f = \mu_f - i\omega\eta_f$, where $\mu$—real part of the shear modulus, $\eta$—viscosity, $\rho$—density, $\omega$—frequency, i—imaginary unit equal to $\sqrt{-1}$, index f refers to a fluid sample under study. Generally, values $\mu$ & $\eta$ represent the "effective" shear modulus and "effective viscosity" and are dependent on the frequency $\omega$.

As a target case, a problem of a torsional wave propagation in an infinite tube filled up with a visco-elastic material, at a radially symmetric disturbance field, was studied, and the correlation between the above-mentioned problem and the problem of defining resonance properties of torsional oscillations of the finite tube section. On the one side, the tube is a container for a sample, on the other side, the tube is a resonance system whose natural oscillations are defined by its geometry and dimensions. By selecting an optimum ratio between the tube length and its diameter & thickness, at a selected tube material, we attain that a torsional resonance will be as far as possible from spurious resonances (bending resonances, etc.), i.e. we will decrease measurement accuracy and, simultaneously, enhance the factor-of-merit and, consequently, the accuracy of the claimed method for measuring visco-elastic fluid properties.

On implementation of the method is where torsional oscillations are excited in the tube section by a source of harmonic current. Amplitude-vs-frequency response values are defined for the first mode of oscillations. This is selected due to the fact that torsional waves of the first oscillation mode propagate without dispersion, whilst waves of succeeding modes propagate with dispersion, i.e. the wave propagation velocity depends on frequency. Thereafter, amplitude of oscillations is recorded, dependent on the excitation frequency, i.e. the whole resonance curve is tracked (near the resonance frequency, the curve may be non-symmetrical). The width of the resonance curve allows the attenuation to be determined. Based on the data received, resonance frequency $\omega_r$ and attenuation coefficient $\alpha$ are determined. After that, the tube is filled with visco-elastic fluid under study, and the resonance frequency shift $\Delta\omega_r$ and attenuation variance $\Delta\alpha$ is measured.

The tube section is a major part of a sophisticated resonator, which, in addition to the tube, includes a bottom with transmitting and receiving systems attached thereto. For the tube section, the lowest resonance frequency is $\omega=\pi c_s/L$, where $c_s$—velocity of transverse waves in the tube ($c_s$ is virtually independent from the frequency), L—tube length. The availability of the bottom with the transmitting and receiving systems may be taken into consideration by modeling it like a discrete mass, which give a small correction to the resonance frequency value.

Within the frames of the suggested theoretical model, a correlation between the real and imaginary parts of a shear modulus of elasticity of the sample $G_f=\mu_f-i\omega\eta_f$ vs resonance frequency shift $\Delta\omega_r$ and variation of torsional oscillation's attenuation factor $\Delta\alpha$ was established:

$$\eta_f \rho_f = -\frac{\Delta\omega_r \Delta\alpha}{2\omega_r}(\rho_s R_1((R_2/R_1)^4 - 1))^2, \quad (1)$$

$$\mu_f \rho_f = \frac{\Delta\alpha^2 - \Delta\omega_r^2}{4}(\rho_s R_1((R_2/R_1)^4 - 1))^2, \quad (2)$$

where $R_{1,2}$.—inner and outer diameters of the tube, indices f & s are referred to fluid sample and tube material.

The validity of the received correlations may be confirmed by studying the Newton fluid, which is known to not have a shear elasticity ($\mu_f=0$) i.e., for defining the viscosity, it's sufficient enough to meter one of the values—frequency shift or attenuation variance. Then, $\Delta\alpha=-\Delta\omega$, and the function looks like that:

$$\eta_f \rho_f = \frac{(\Delta\omega_r)^2}{2\omega_0}(\rho_s R_1((R_2/R_1)^4 - 1))^2 \quad (3)$$

$$= \frac{(\Delta\alpha)^2}{2\omega_0}(\rho_s R_1((R_2/R_1)^4 - 1))^2.$$

An experimental unit (see. FIG. 1) was used to implement the suggested method.

The sample under examination (1) was placed into an aluminum tube with a bottom. The tube was hanged vertically in the air chamber (3) with thermostabilization capability to maintain constant temperature of measurements and, therefore, the accuracy of the experiment, since the viscosity of the material is a variable that to a great extent depends on a temperature. The chamber (3) is designed as a cylinder with outer thermal insulation, with a hollow side wall, in which cooling fluid injected by the thermostat (5) circulates. The cooling fluid temperature in the thermostat was automatically controlled by the outer transducer (4) placed in the chamber (3). To provide a more uniform thermostabilization bahavior, a microfan was installed in the chamber (3). Within the range of temperatures used in the measuring process (−10÷60° C.), the accuracy of the temperature value maintained in the chamber (3) was 0.1° C.

Figure 3:
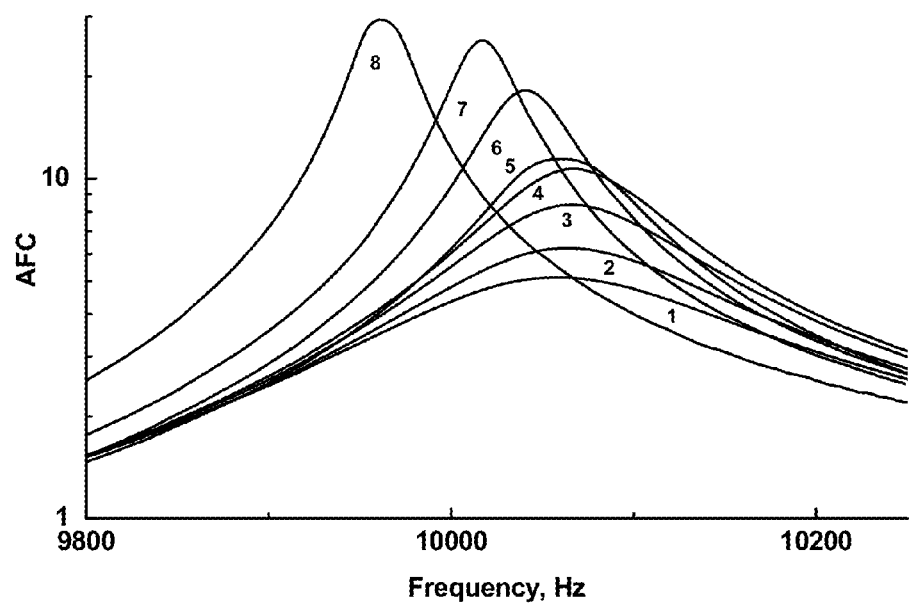

While measuring, it was necessary to take into consideration that temperature variation results in a shift of the resonance frequency and the hollow tube, since its length and shear wave velocity in the tube material changes. Test results for a hollow tube are shown in FIG. 3.

For contact-free acoustic measurements, i.e., to minimize the suspension impact on resonance properties, the tube was banded with a thin fiber in the middle, i.e. along the line of the node of the first mode of torsional oscillations (this line, in fact, is an outer boundary of the tube's cross-section plane, equally-spaced from the tube ends), and suspension fibers were attached to this fiber.

Torsional oscillations were excited in the vicinity of the first natural torsional resonance. Oscillations were excited by two point power sources, i.e., the transmitting transducers (piezoelectric accelerometers), which are positioned diametrically opposed to each other on the resonance device's side wall, at the bottom level (in other words, if a tube is used, on the circumference of the tube bottom). The accelerometer's axis of sensibility was parallel to a tangent line to the resonance device surface at the accelerometer's point of contact, whilst the accelerometers themselves were oriented in the opposite direction.

The third accelerometer (a receiving transducer, located similar to the transmitting transducers, was positioned on the resonance device's side wall, at the bottom level, at a distance equally remote from the transmitting transducers) was used to record a signal (in other words, in situations where a tube is used, on the tube bottom circumference, in the middle between them).

For receiving a resonance curve of torsional oscillations, a programmable, frequency-adjustable, sine signal generator (6), signal preamplifier and analog-to-digital converter (A/D converter) (7) were used. The generator and A/D converter were controlled from the computing device (computer) (8), using the Matlab software. Each point of the measuring system's frequency-response curve was calculated on-line as a relation of spectral components of a given frequency for a signal registered by the receiver as well as for a signal sent to the transmitting transducer.

The accuracy of the suggested measuring system is defined by a distance of oscillation modes of other types (bending, bell-shaped, second, third modes of torsional oscillations) away from the used first mode of torsional oscillations (which is, in fact, the effective resonance of the system), which, within the frames of the claimed invention, are assumed as the "spurious" resonance.

For defining a spectrum of natural frequencies and for minimizing the impact of spurious resonances, a finite element method was used for the tube oscillation simulation and Comsol software was applied to select geometry. Comsol software is a software tool applied to perform thermal, acoustic, electrical, chemical and other calculations. Visit website http://www.comsol.com to receive detailed information on the software.

Therefore, by selecting geometry of the tube, namely, the relationship between the length and inner & outer radius for the selected tube material, we will remove the effective resonance away from spurious resonances as far as possible. At the same time, while defining absolute dimensions of the resonance device and fulfilling the ratio between geometric parameters (length vs inner & outer diameters for the selected tube material), it will be possible to implement the method at a required effective resonance frequency (e.g., a value from acoustic logging frequency range (5-20 kHz)).

The below-mentioned simulation results are presented as an example that illustrates the possibility of removing spurious resonances from the effective one dependent on the tube geometry, in particular, for a case when the tube length varies while other selected dimensions remain constant.

The inner and outer radiuses of the tubes were 12.9 mm and 16.7 mm, respectively, the bottom thickness was 1 mm, and the only difference was the length (149.6 mm and 74.8 mm); they were selected in a way to allow measurement of viscoelastic properties at frequencies of 10 and 20 kHz. Density of the aluminum alloy, which was used for tube fabrication, was 2.78 g/cm$^3$.

A rubber-like viscous and elastic material with a shear module within $10^5 \div 10^6$ Pa and Poisson ratio of 0.48 was used as Specimen 1.

For the long tube (149.6 mm), the following natural frequencies were received through simulation: 6.5÷6.6 kHz (spurious resonance), 10 kHz (effective resonance) and 11.3÷14 kHz (spurious resonance). For the short tube (74.8 mm), similar frequencies were virtually independent from the specimen shear modulus, standing at 18.9 kHz (spurious resonance), 19.8 kHz (effective resonance) and 23.3 kHz (spurious resonance). Therefore, the used torsional resonance was removed away from the nearest resonances of other modes by 1.3 kHz for the long tube and by 0.9 kHz for the short tube, i.e. the long tube in the example under consideration was the most acceptable one.

The above-mentioned example illustrates the spurious-vs-effective resonance position for a case when the tube length is the only variable, at the selected inner & outer diameters for the given tube material. It's easy to understand that the above-mentioned software simultaneously processes a number of required parameters (parameter selection) with the aim of finding an optimum relationship between them.

Figure 4:
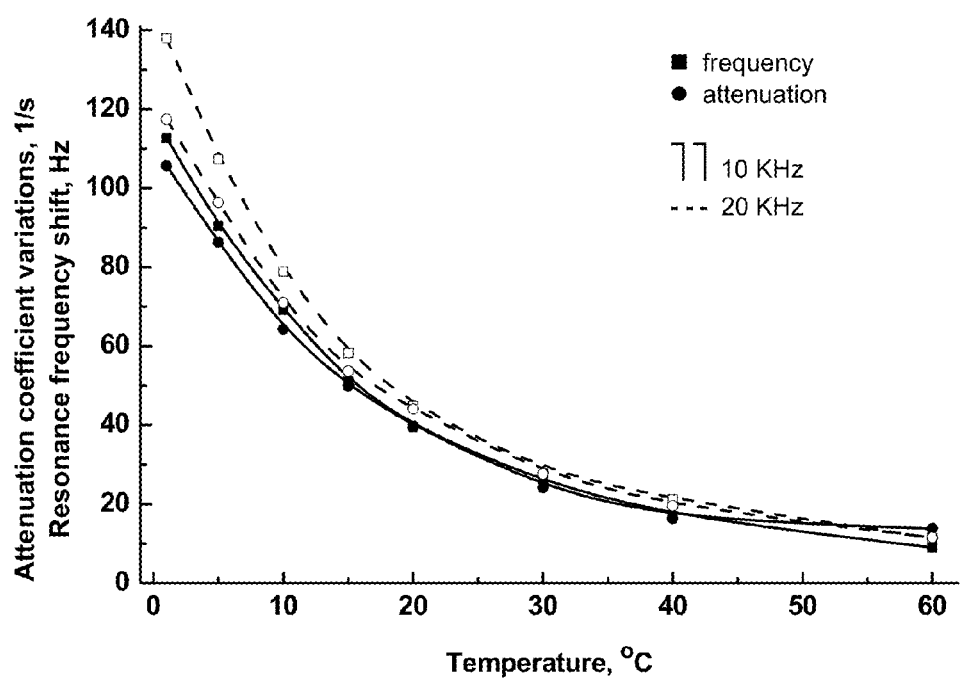

To verify the compliance between the theoretical description and experimental data received, test measurements were conducted for glycerin, i.e., for a fluid that does not have any shear modulus of elasticity within the studied frequency & temperature range. An amplitude-vs-frequency response curve for a tube with a resonance frequency of 10 kHz is shown in FIG. 3. Frequency shift and oscillation attenuation variance for a glycerin-filled tube is shown in FIG. 4.

Figure 5:
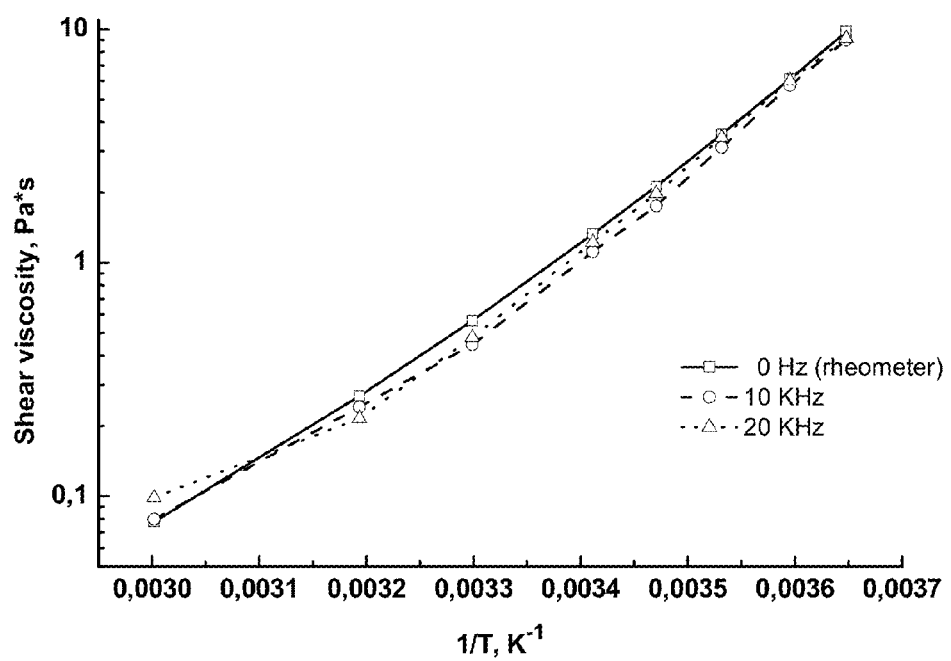
Figure 6:
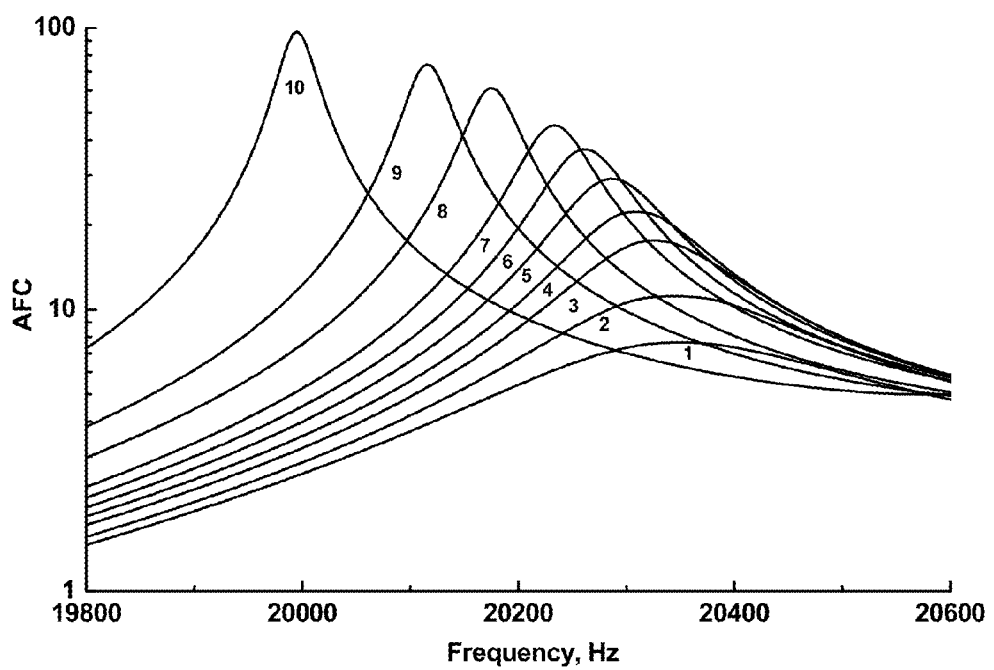

In situations where there is no shear modulus (for Newton fluid), the frequency shift and attenuation variance are equal to each other and, therefore, the curves shown in FIG. 5 should coincide. However, the difference between the curves received is likely to be explained by an incompletely adequate approximation of the contribution of other modes by a frequency-independent summand and is considered as a systematic measurement error. As follows from FIG. 5, the above-mentioned error is higher for a measuring system in which a shorter tube is used. For a 10 kHz measuring system, the error is 6% and reaches 15% for a 20 kHz measuring system.

The glycerin viscosity calculation as per Formula (3) brought the results, which are close to values obtained during viscosity measurement, using a standard rotary rheometer. The results are presented in FIG. 5, where viscosity is plotted in coordinates, which show that Arrhenius law is fulfilled for glycerin, i.e. the viscosity logarithm vs reverse temperature curve is a straight line. The viscous flow activation energy for glycerin, calculated based on experimental data in accordance with Arrhenius law, was 68 kJ/mol, which is close to the spreadsheet value of 63±4 kJ/mol.

Thus, experimental data received for glycerin (a Newton fluid, i.e. fluid with a zero real part of shear modulus of elasticity)—attenuation curve and resonance frequency curve, which coincide with each other (with adjustment for error) at all temperatures—confirm the validity of using the established relationship (1), (2) for defining parameters of visco-elastic fluids.

The advantage of the suggested measuring method is that frequency and attenuation shift are independent from the tube length, i.e., from a resonance frequency of torsional oscillations, measurements do not require any data on the tube material shear modulus. Measuring the sample density and tube material is the only thing additionally needed.

Within the frames of the claimed invention, the known data on the specimen density vs temperature relation was assumed as a prerequisite.

The density vs temperature curve of the test fluid was defined using Archimedes principle. A weight of silica glass of a calibrated volume (10.000±0.005 cm$^3$) was first weighed in the air and then in the fluid under examination, whose temperature was maintained constant with an accuracy of 0.1° C. in a range of 0÷40° C. A thermocouple, which ensures the specified measurement accuracy, was used to control the test fluid temperature. The scale accuracy was 0.0001 g. A thermostat-connected coil, which embraces a cup filled with the test fluid and which provides a heat insulation coating (foam) from outside, was used for thermostabilization purpose. Within the measurement accuracy limits, the temperature curves for both used fluids (glycerin and oil) may be assumed as a linear function. The density vs temperature curves for glycerin $\rho_{gl}$(T) and the Mordovo-Karmalskoye field oil $\rho_{oil}$(T), which was used as a test fluid, were as follows:

$$\rho_{gl}(T)=127.70\pm0.3-(0.71\pm0.02)\cdot T$$

$$\rho_{oil}(T)=95.93\pm0.2-(0.74\pm0.007)\cdot T'$$

where density is expressed in kg/m$^3$, temperature is expressed in ° C.

Here is an example of the implementation of the claimed resonance method for measuring visco-elastic fluid parameters for a case if the Mordovo-Karmalskoye field oil is used as a test fluid. The results of the experiments are presented in FIG. 6, 7, 8, 9.

At the established constant temperature of 20° C., a continuous time-variant signal at a frequency of 19,800-20,600 Hz was generated in the thermostabilized air chamber (3) by the sine signal generator (6) and was sent to the transmitting transducers (point power sources) located on a hollow tube, which, in its turn, excited torsional oscillations. The relationship of geometric parameters of the tube, i.e., length and inner & outer radiuses, as well as the selected tube material were as follows: tube length—75 mm, inner radius—12.9 mm, outer radius—16.7 mm, material—aluminum alloy with a density of 2.78 g/cm$^3$.

The third accelerometer positioned on the bottom circumference in the middle between the transmitting transducers was used to record torsional oscillations. As a result, an amplitude-vs-frequency response curve was received, based on which the resonance frequency value $\omega_r$=20,269.5 Hz and the attenuation ratio value $\alpha$=8.1 s$^{-1}$ were established; to define the values, a resonance curve simplex approximation method was used.

Thereafter, the tube was filled up with the Mordovo-Karmalskoye field oil. The oil density calculated as per formula: $\rho_{oil}(T)$=95.93±0.2−(0.74±0.007)·T, was 974 kg/m$^3$.

While changing the frequency from 19,800 Hz to 20,600 Hz, which is sent from the sine signal generator (6) to the transmitting transducers, an amplitude-vs-frequency response curve was also obtained for the oil-filled tube. Based on the relationship obtained, the resonance frequency $\omega_r$=20,232.3 Hz and the attenuation factor $\alpha$=34.1 c$^{-1}$ were defined.

Therefore, the resonance frequency shift is $\Delta\omega_r$=−37.2 Hz and the attenuation variance is $\Delta\alpha$=26 c$^{-1}$.

Formulas (1) & (2) were applied to calculate the real part of the shear modulus (storage modulus) $\mu$ and effective viscosity $\eta$, which make it possible to determine target "effective" visco-elastic properties of the specimen at the first torsional resonance frequency $\omega_r$. These values at a temperature of 20° C. were as follows: $\mu$=14,630 Pa and $\eta$=0.364 Pa*s.

Similar measurements were conduced at other temperatures from a range of −10 . . . +60° C. A frequency-response curve was picked up three times for each temperature, and the repeatability error did not exceed 0.3%.

Figure 7:
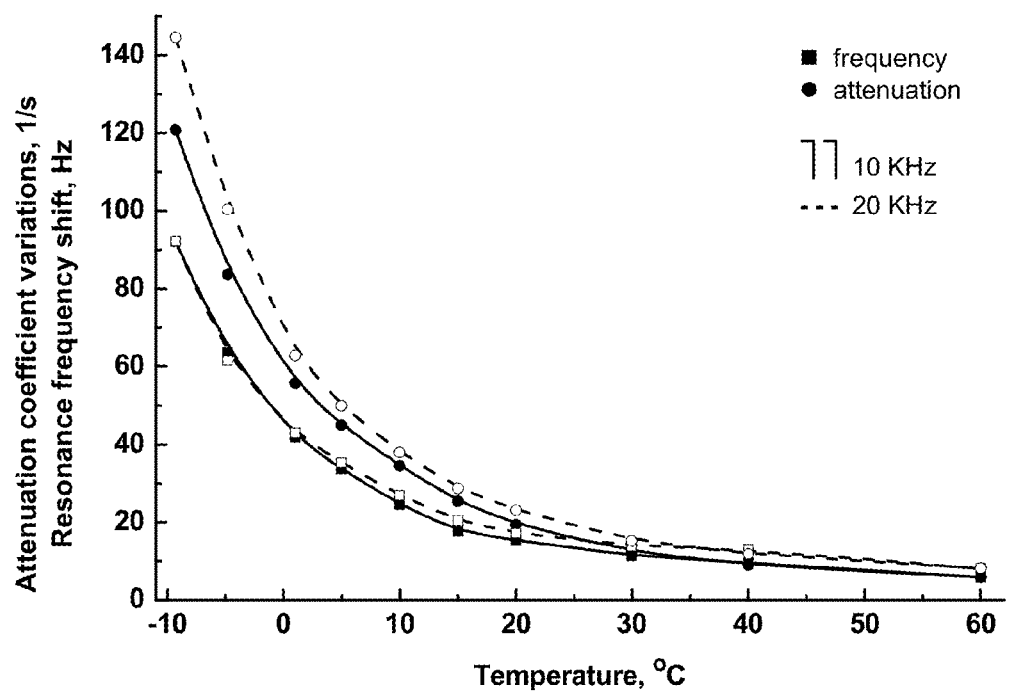
Figure 8:
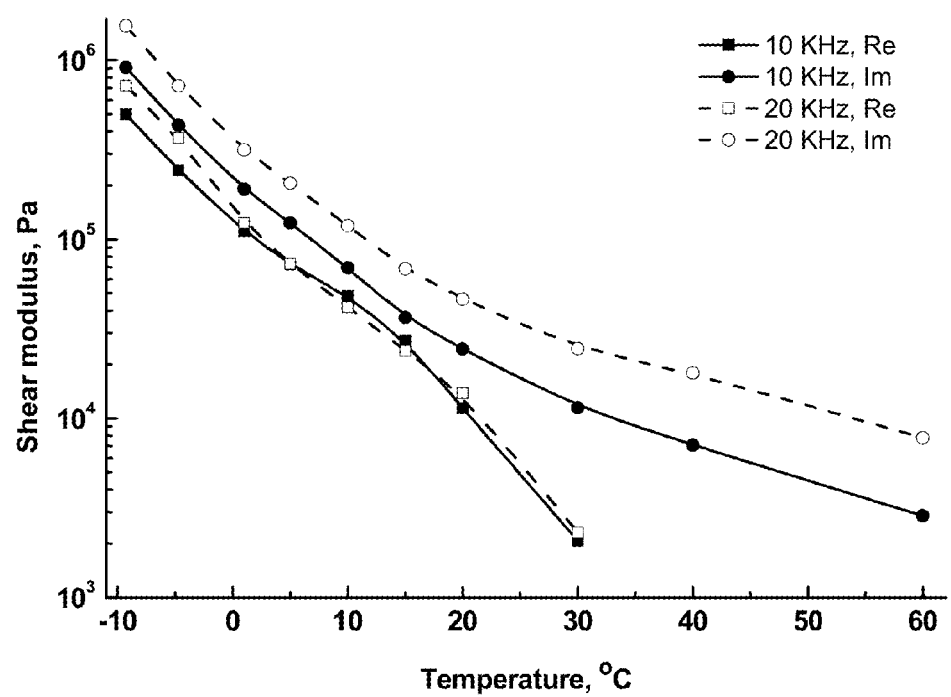

A pattern of the curves received (FIG. 7, FIG. 8) evidences that the studied oil showed its visco-elastic properties at temperatures below 20° C. The shear modulus' real part is not presented for temperatures above 30° C., since the modulus values are comparable with the measurement accuracy.

Figure 9:
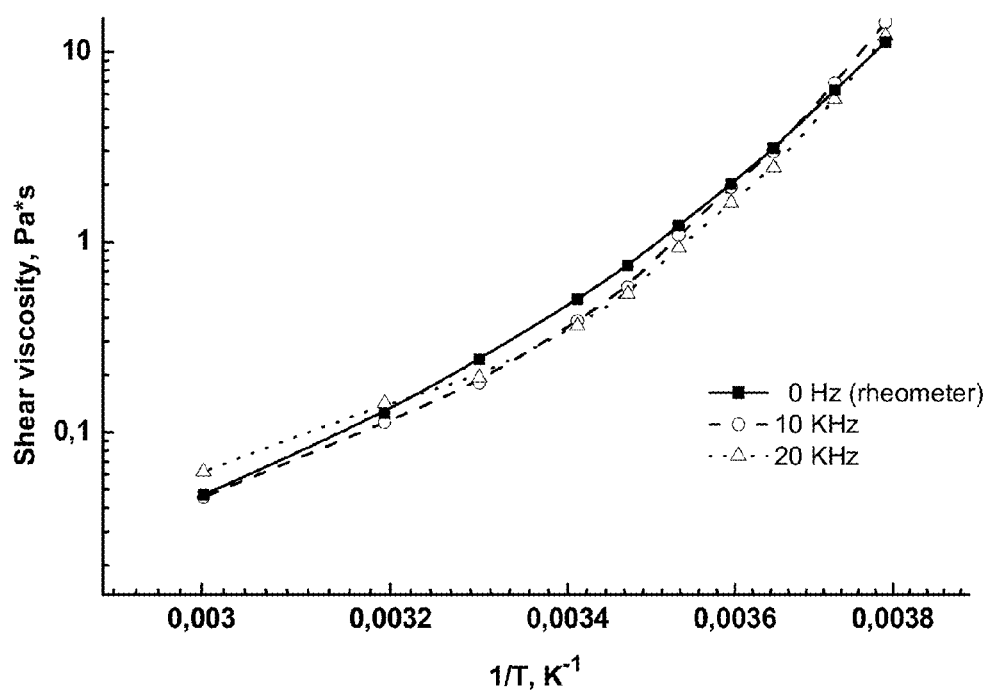

The viscosity-vs-temperature curve illustrated in FIG. 9 shows that the studied oil properties deviated from the Arrhenius law that is typical for vitrifying fluids. The viscous flow activation energy is 38 kJ/mol for a high temperature (60° C.) and 78 kJ/mol for a low temperature (−9.3° C.).

The suggested measuring method may be used in industrial units for on-line study of properties of visco-elastic fluid samples, passing through tubes under increased pressure.

The invention claimed is:

1. A method for measuring visco-elastic fluid properties comprising the steps of:
    providing a hollow axially symmetric resonance device disposed vertically in a thermostabilized chamber, the resonance device dimensions and material selected so as to minimize the impact of oscillation modes, which differ from an effective resonance, on the said effective resonance,
    sending a continuous variable-frequency signal to at least two transmitting transducers located on an outer surface of the resonance device thus exciting the resonance device torsional oscillations,
    recording oscillations by at least one receiving transducer, located on the outer surface of the resonance device,
    plotting an amplitude-vs-frequency response curve by the first oscillation mode and determination of the effective resonance frequency $\omega_r$,
    filling a cavity of the said resonance device with a medium under examination,
    sending a continuous variable-frequency signal to the transmitting transducers thus exciting the medium-filled resonance device oscillations,
    recording oscillations by at least one receiving transducer, located on the outer surface of the medium-filled resonance device,
    plotting an amplitude-vs-frequency response curve for the said medium-filled resonance device and determination of the effective resonance frequency $\omega_r$,
    defining attenuation factor $\alpha$ for the empty and test medium-filled resonance device,
    defining the resonance frequency shift $\Delta\omega_r$ and the attenuation variance $\Delta\alpha$ in relation to the hollow resonance device, whilst the real part of the shear modulus $\mu$ and dynamic viscosity $\eta$ are calculated, using the formulas specified below:

$$\eta_f(\omega_r)\rho_f = \frac{\Delta\omega_r \Delta\alpha}{2\omega_r}(\rho_s R_1((R_2/R_1)^4 - 1))^2,$$

$$\mu_f(\omega_r)\rho_f = \frac{\Delta\alpha^2 - \Delta\omega_r^2}{4}(\rho_s R_1((R_2/R_1)^4 - 1))^2,$$

where $\omega_r$—resonance frequency value for an empty capacity (no fluid), $\Delta\omega_r$—resonance frequency shift, $\Delta\alpha$—attenuation variance, $\rho$—density, $R_1$ & $R_2$ inner and outer radiuses of the capacity, respectively; lower indices f and s refer to fluid and capacity, respectively.

2. The method of claim 1, wherein the transmitting transducers are positioned diametrically opposed on the resonance device's side wall at the bottom level.

3. The method of claim 1, wherein absolute dimensions of the resonance device are determined at the established relationship between its length and inner and outer radiuses and a selected material of the resonance device.

4. A device for measuring visco-elastic fluid parameters, comprising:
    an axially symmetric resonance device disposed vertically within a thermostabilized chamber and being hanged along the line of the node of the first mode of torsional oscillations, the resonance device dimensions and material are selected so as to minimize the impact of oscillation modes, which differ from the effective resonance, on the said effective resonance,
    at least two transmitting transducers and at least one receiving transducer located on the resonance device's outer surface,
    a computer,
    a sine wave generator connected to the said computer and having an output connected to the transmitting transducers,
    an analog-to-digital converter connected to the said computer and having an input connected to the receiving transducer.

5. The device of claim 4, wherein the axially symmetric resonance device is a tube.

6. The device of claim 4, wherein transmitting transducers are disposed diametrically opposed to each other on the resonance device's side wall at the bottom level.

7. The device of claim 4, wherein the receiving transducer is disposed on the resonance device's side wall at the bottom level, at a distance equally remote from the transmitting transducers.

8. The device of claim 4, wherein the receiving transducer is connected to the input of the analog-to-digital converter via a signal amplifier.

9. The device of claim 4, wherein the thermostabilized chamber is of an air type.

10. The device of claim 4, wherein the thermostabilized chamber is made with a cylinder-shaped side wall.

11. The device of claim 4, wherein the side wall is hollow.

12. The device of claim 4, wherein the hollow side wall is filled with a cooling fluid.

13. The device of claim 4, wherein the thermostabilized chamber is provided with a microfan.

14. The device of claim 4, wherein the thermostabilized chamber is provided with a temperature transducer.

15. The device of claim 4, wherein the temperature transducer is connected to a thermostat.

16. The device of claim 4, wherein absolute dimensions of the resonance device are changed at the established relationship between its length and inner & outer radius for a selected material.

* * * * *